United States Patent
Peloux et al.

(10) Patent No.: US 9,746,693 B2
(45) Date of Patent: Aug. 29, 2017

(54) SYSTEM COMPRISING A MULTIFOCAL DIFFRACTIVE LENS COMPONENT

(71) Applicants: ESSILOR INTERNATIONAL (COMPAGNIE GENERALE D'OPTIQUE), Charenton-le-pont (FR); CENTRE NATIONAL DE LA RECHERCHE SCIENTIFIQUE (CNRS), Paris (FR)

(72) Inventors: Marius Peloux, Charenton-le-Pont (FR); Pierre Chavel, Palaiseau (FR)

(73) Assignees: ESSILOR INTERNATIONAL (COMPAGNIE GENERALE D'OPTIQUE), Charenton-le-Pont (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 113 days.

(21) Appl. No.: 14/437,341

(22) PCT Filed: Oct. 23, 2013

(86) PCT No.: PCT/EP2013/072196
§ 371 (c)(1),
(2) Date: Apr. 21, 2015

(87) PCT Pub. No.: WO2014/064163
PCT Pub. Date: May 1, 2014

(65) Prior Publication Data
US 2015/0286071 A1    Oct. 8, 2015

(30) Foreign Application Priority Data
Oct. 23, 2012    (EP) ..................... 12306314

(51) Int. Cl.
*G02C 7/00* (2006.01)
*G02C 7/02* (2006.01)
(Continued)

(52) U.S. Cl.
CPC ............ *G02C 7/042* (2013.01); *A61F 2/1602* (2013.01); *G02B 5/1895* (2013.01); *G02C 7/022* (2013.01);
(Continued)

(58) Field of Classification Search
CPC  G02B 5/1895; G02B 5/1876; G02B 27/0075; G02B 27/58; G02C 7/02;
(Continued)

(56) References Cited

U.S. PATENT DOCUMENTS

| | | | |
|---|---|---|---|
| 5,114,220 A | 5/1992 | Baude et al. | |
| 2004/0156014 A1* | 8/2004 | Piers ................... | A61B 3/0025 351/159.41 |
| 2009/0195748 A1* | 8/2009 | Bandhauer ............ | A61F 2/1618 351/159.47 |

FOREIGN PATENT DOCUMENTS

| | | | |
|---|---|---|---|
| EP | 0 109 753 A2 | 5/1984 | |
| EP | 0 335 731 A2 | 10/1989 | |

(Continued)

OTHER PUBLICATIONS

International Search Report, dated Jan. 22, 2014, from corresponding PCT application.

*Primary Examiner* — Scott J Sugarman
*Assistant Examiner* — Mustak Choudhury
(74) *Attorney, Agent, or Firm* — Young & Thompson (57) ABSTRACT

A system includes a simultaneously bifocal diffractive lens component having a first focal point, a second focal point and a plurality of diffractive zones including a central zone and a plurality of annular concentric zones surrounding the (Continued)

central zone, the lens component having a first optical power and a second optical power associated with the first and second focal points respectively, the first and second focal points respectively corresponding to points of convergence of the most luminous orders of diffraction generated by the lens component for a nominal wavelength, the first system focal point and the second system focal point having a position dependent upon the value of the first optical power and the second optical power of the lens respectively, the central zone having a surface area value determined as a function of the pupil of the optical system, of the first optical power and the second optical power.

19 Claims, 5 Drawing Sheets

(51) Int. Cl.
*G02C 7/04* (2006.01)
*G02B 5/18* (2006.01)
*G02C 7/06* (2006.01)
*A61F 2/16* (2006.01)

(52) U.S. Cl.
CPC ............... *G02C 7/028* (2013.01); *G02C 7/06* (2013.01); *G02C 7/065* (2013.01); *G02C 2202/20* (2013.01)

(58) Field of Classification Search
CPC ........ G02C 7/041; G02C 7/042; G02C 7/044; G02C 7/06; G02C 7/022; G02C 7/028; G02C 2202/20; A61F 2/1602; A61F 2/1613; A61F 2/16
USPC .................. 351/54, 55, 159.01–159.74, 228; 359/238, 565–574, 741; 623/5.11, 6.11, 623/6.17, 6.3, 6.22
See application file for complete search history.

(56) References Cited

FOREIGN PATENT DOCUMENTS

| | | |
|---|---|---|
| EP | 0 343 067 A1 | 11/1989 |
| EP | 0 537 643 A1 | 4/1993 |
| EP | 0 367 878 A1 | 5/1999 |
| WO | 00/20903 A1 | 4/2000 |
| WO | 2006/036762 A2 | 4/2006 |
| WO | 2009/005822 A1 | 1/2009 |

\* cited by examiner

SYSTEM COMPRISING A MULTIFOCAL DIFFRACTIVE LENS COMPONENT

BACKGROUND OF THE INVENTION

Field of the Invention

The present invention concerns a system comprising a multifocal diffractive lens component. In particular the invention relates to a system comprising a diffractive lens component configured to be simultaneously bifocal. The invention further relates to a method of determining a simultaneously bifocal diffractive system comprising a lens component.

Applications of the present invention can be found in the fields of vision improvement and correction of vision defects. Ophthalmic lenses are worn and widely used for the correction of various types of vision deficiencies. These include defects such as near-sightedness (myopia), farsightedness (hypermetropia), astigmatism, and defects in near-range vision usually associated with aging (presbyopia).

In the context of the present invention the term ophthalmic lens refers to vision correction lens such as a spectacle lens, a contact lens, an intraocular lens, an artificial cornea and the like.

Description of the Related Art

Ophthalmic lens include multifocal lenses in which a first region of the lens is designed to have a first focal length and another different region of the lens is designed to have a second focal length different to the first focal length. Typically one of the focal lengths corresponds to a focal length for viewing far objects and another focal length corresponds to a focal length for viewing near objects. Accordingly, a near vision (NV) zone corresponds to the surface area of the ophthalmic lens including the points of intersection of the lines of sight of the user for near distance vision such as reading and the far vision zone (FV) corresponds to the surface area of the ophthalmic lens including the points of intersection of the lines of sight of the user for far distance vision for viewing distant objects. Such multifocal ophthalmic lens include bifocal lenses having a far vision zone and a near vision zone and progressive lenses which have a far vision zone, a near vision zone, and an intermediate zone between the far vision zone and the near vision zone, with a principal progression meridian crossing the three zones. Multifocal lenses are often used for the correction of vision defects caused by presbyopia.

Other types of bifocal lens are configured for simultaneous bifocal vision.

In some cases such lenses have an inner zone having a first focal length and an outer annular zone surrounding the inner zone having a second different focal length. Light passing through the inner zone forms an image at the first focal length and light passing through the outer zone forms an image at the second focal length. One of the images is projected onto the retina of the eye of the user while the other image is simultaneously projected behind or in front of the retina. The human brain processes the visual signals received in such a way that the improperly focused image is ignored thereby giving the user the impression of one focused image.

The design of such lens provides many challenges in terms of quality of vision.

SUMMARY OF THE INVENTION

The present invention has been devised to address one or more of the foregoing concerns.

According to a first aspect of the invention there is provided a simultaneously bifocal optical system, the said optical system being defined by a first system focal point and a second system focal point and a pupil, said system comprising a simultaneously bifocal diffractive lens component having a first focal point, a second focal point and a plurality of diffractive zones, the plurality of diffractive zones including a central zone and a plurality of annular concentric zones surrounding the central zone, the lens component having a first optical power P1 and a second optical power P2 associated with the first focal point and the second focal point respectively, the first focal point and the second focal point respectively corresponding to points of convergence of the most luminous orders of diffraction generated by the lens component for a nominal wavelength, the first system focal point and the second system focal point having a position dependent upon the value of the first optical power P1 and the second optical power P2 of the lens respectively, wherein the central zone has a surface area value configured such that a predetermined optical performance optimisation parameter $\phi$ is optimised, said optical performance optimisation parameter $\phi$ being considered in the vicinity of the first and second system focal points and varying as a function of the surface area value of the central zone without modifying the operational function of the diffractive zones, said predetermined optical performance optimisation parameter $\phi$ being such as the brightness and/or the Modulation Transfer Function in the vicinity of the first and second system focal points, whereby the central zone has a surface area value determined as a function of the pupil of the optical system, of the first optical power P1 and of the second optical power P2.

In an embodiment, each of the plurality of diffractive zones has a spherical profile or is of a binary type. A spherical profile corresponds to a hyperbolic phase function generating a spherical wavefront.

In an embodiment, the pupil of the optical system has a variable surface area value.

In an embodiment, the pupil of the optical system has a fixed surface area value.

In an embodiment, the lens component is configured as a contact lens. In another embodiment, the component is part of an intraocular implant.

In some embodiments the lens component constitutes the optical system.

In an embodiment, the lens component is part of a near vision zone of a progressive, multifocal ophthalmic lens having a complex surface comprising a far vision zone with a far vision reference point, said near vision zone with a near vision reference point, and an intermediate vision zone wherein a main meridian of the progression crosses the three said vision zones, wherein the first optical power P1 differs from the second optical power P2.

Figure 2:
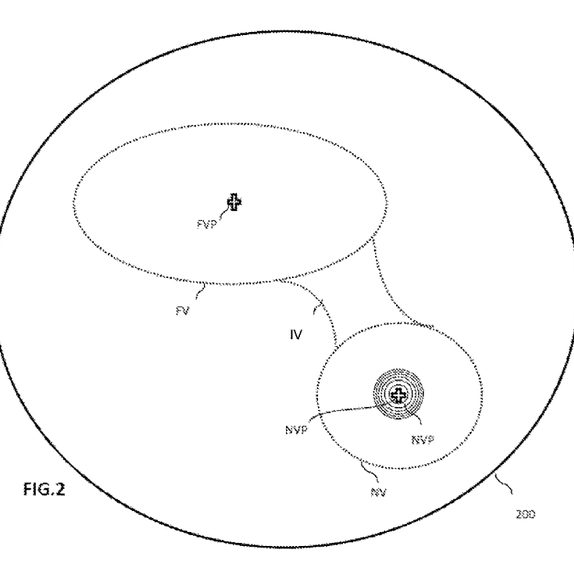
FIG. 2 is a schematic planar diagram of an ophthalmic lens system from above according to one or more embodiments of the invention.

In an embodiment, the lens component comprises a refractive component and a simultaneously bifocal diffractive component in which the refractive component is juxtaposed with the diffractive component and wherein the refractive component has an optical power equal to P1/2+P2/2 and the diffractive component has a first power equal to $\Delta P/2$ and a second power equal to $-\Delta P/2$, where $\Delta P = P1 - P2$. An example of such an embodiment is shown in FIG. 2.

In an embodiment, the first optical power P1 is positive and the second optical power P2 is zero.

A second aspect of the invention provides a method of determining a simultaneously bifocal diffractive optical system, the said optical system being defined by a first system focal point and a second system focal point and a pupil, said system comprising a lens component having a first focal point, a second focal point and a plurality of diffractive zones, the plurality of diffractive zones including a central zone and a plurality of annular concentric zones surrounding the central zone, the lens component having a first optical power P1 and a second optical power P2 associated with the first focal point and the second focal point respectively, the first focal point and the second focal point respectively corresponding to points of convergence of the most luminous orders of diffraction generated by the lens component for a nominal wavelength, the first system focal point and the second system focal point having a position dependent upon the value of the first optical power P1 and the second optical power P2 of the lens respectively, wherein the method comprises a step of determining a surface area value of the central zone by optimisation of a predetermined optical performance optimisation parameter φ, said optical performance optimisation parameter φ being considered in the vicinity of the first and second system focal points and varying as a function of the surface area value of the central zone without modifying the operational function of the diffractive zones, said predetermined optical performance optimisation parameter φ being such as the brightness and/or the Modulation Transfer Function in the vicinity of the first and second system focal points, whereby the surface area value of the central zone is determined as a function of the pupil of the optical system, of the first optical power P1 and of the second optical power P2.

In an embodiment, the component constitutes the optical system.

In an embodiment, the pupil of the optical system has a fixed surface area value and the step of determining the surface area value of the central zone by optimisation of the optical performance optimisation parameter φ is carried out in considering the pupil surface area value.

In an embodiment, the pupil of the optical system has a surface area value variable within a range of surface area values and wherein the step of determining the surface area value of the central zone comprises:

evaluating surface area values of the central zone, associated with a set of pupils of the said optical system, each pupil having a surface area value within the said range of surface area values, by optimisation of the optical performance optimisation parameter φ for each pupil of this set;

evaluating an optical performance of the optical system for each of the surface area values of the central zone as a mean of the optimised optical performance optimisation parameters φ on the set of pupil surface area values of the said optical system; and determining an optimum performance among the evaluated optical performances of the said optical system and deducing therefrom the surface area value of the central zone which corresponds to the determined optimum performance.

In an embodiment, the optical performance optimisation parameter φ is based on the Modulation Transfer Functions at the system focal planes associated with the first and second focal points.

In an embodiment, the optical performance optimisation parameter φ is based on the brightness level in the vicinity of the first and second system focal points of the said optical system.

At least parts of the methods according to the invention may be computer implemented. Accordingly, the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, the present invention may take the form of a computer program product embodied in any tangible medium of expression having computer usable program code embodied in the medium.

Since some parts of the present invention can be implemented in software, the present invention can be embodied as computer readable code for provision to a programmable apparatus on any suitable carrier medium. A tangible carrier medium may comprise a storage medium such as a floppy disk, a CD-ROM, a hard disk drive, a magnetic tape device or a solid state memory device and the like. A transient carrier medium may include a signal such as an electrical signal, an electronic signal, an optical signal, an acoustic signal, a magnetic signal or an electromagnetic signal, e.g. a microwave or RF signal.

BRIEF DESCRIPTION OF THE DRAWING FIGURES

Embodiments of the invention will now be described, by way of example only, and with reference to the following drawings in which.

DETAILED DESCRIPTION OF THE INVENTION

Figure 1:
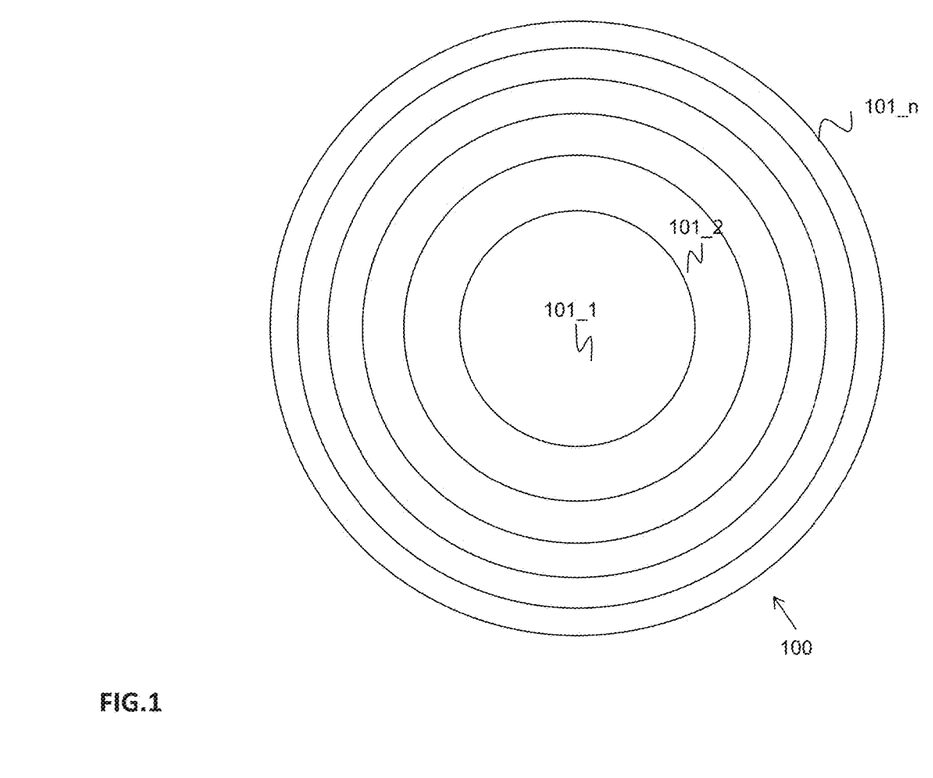
FIG. 1 is a schematic planar diagram from above of an optical lens component according to one or more embodiments of the optical system of the invention.

An ophthalmic lens component in accordance with one or more embodiments of the optical system of the invention is illustrated in FIG. 1. The ophthalmic lens component 100 comprises a diffractive zone plate comprising a plurality of diffractive zones 101_1 to 101_n including a central zone 101_1 surrounded by a plurality of annular concentric zones 101_2 to 101_n.

The number of diffractive zones n depends on factors such as the size of the ophthalmic lens component, the variation of the base optical power and the operational wavelength. The ophthalmic lens component is configured to be simultaneously bifocal and has a first focal point f1 and a second focal point f2, associated with a first optical power P1 and a second optical power P2, respectively. The first focal point f1 and the second focal point f2 correspond to the brightest orders of diffraction generated by the ophthalmic lens component 100 for a given wavelength of light. The positions of the first focal point f1 and the second focal point f2 are respectively dependent upon the value of the first optical power and the second optical power of the lens. The surface area of the central diffractive zone 101_1 is determined as a function of the pupil of the optical system in which the ophthalmic lens component is placed, and as a function of the first optical power P1 and the second optical power P2.

The optical system may be an ophthalmic contact lens, an ophthalmic spectacle lens, a progressive addition lens comprising a patch disposed on its near vision zone or an intraocular lens implant.

In some embodiments of the invention each of the diffractive zones $101\_1$ to $101\_n$ has a spherical profile. In other embodiments each of the diffractive zones has a binary type profile.

In one embodiment of the invention the ophthalmic lens component 100 is configured as a contact lens. In another embodiment the ophthalmic lens component 100 is an intraocular implant.

Figure 3:
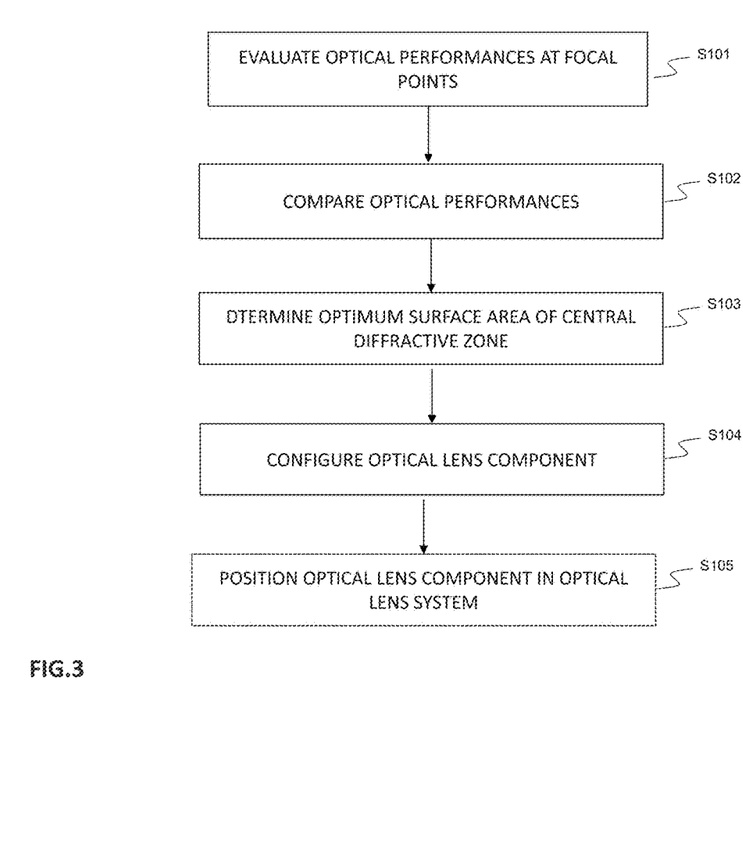
FIG. 3 is a flow chart illustrating steps of a method for determining a design of an optical lens system according to one or more embodiments of the invention.

In one particular embodiment of the invention the ophthalmic lens component 100 is configured to be placed in a simultaneously bifocal optical system, defined by a first system focal point, a second system focal point and a pupil. The positions of the first system focal point F'1 and the second system focal point F'2 depend respectively on the positions of the first focal point f1 and the second focal point f2 of the ophthalmic lens component 100. With reference to FIGS. 2 and 3 a simultaneously bifocal optical system according to one particular embodiment of the invention comprises a progressive multifocal ophthalmic lens having a complex surface comprising a far vision zone FV with a far vision reference point FVP, a near vision zone NV with a near vision reference point NVP and an intermediate vision zone IV defining a progression between the near vision zone NV and the far vision zone FV. A principal meridian of the progression traverses the three vision zones NV, IV and FV. An ophthalmic lens component 100 described with reference to FIG. 1 is juxtaposed in the near vision zone NV.

The ophthalmic lens component placed in the near vision zone NV comprises a refractive component and a simultaneously bifocal diffractive component. The refractive component is juxtaposed with the diffractive component. The refractive component has an optical power equal to P1/2+P2/2 and the diffractive component has a first optical power equal to $\Delta P/2$ and a second optical power equal to $-\Delta P/2$, where $\Delta P=P1-P2$. The first optical power P1 is positive and the second optical power P2 is zero In one embodiment the pupil of the optical system has variable surface profile. In another embodiment the pupil PU has a fixed surface profile.

A method of determining the design of a simultaneously bifocal diffractive ophthalmic lens component in accordance with one or more embodiments of the invention will be described with reference to FIG. 3.

The described method involves optimising the optical performance of an ophthalmic lens system comprising ophthalmic lens component 100. The optical performance may be optimised by optimisation of a performance optimisation parameter $\phi$ which varies as a function of the surface area of the central diffractive zone $101\_1$ in particular, without modifying the operational function of the diffractive zones. The surface area of the central diffractive zone $101\_1$ is determined as a function of the surface of the pupil PU of the ophthalmic lens component 100. In some embodiment the pupil surface is fixed. In other embodiments the pupil of the ophthalmic lens system has a variable surface.

The optical performance of the ophthalmic lens component at the first and second focal points F1 and F2 is considered. Criteria evaluated for optimization of the performance optimization parameter may include optical performance parameters such as the brightness at the focal points F1 and F2 of the ophthalmic lens component 100 and/or the Modulation Transfer Function (MTF) at the focal points F1 and F2 of the ophthalmic lens component.

A main step of the method involves determining the surface area of the central diffractive zone $101\_1$ for optimised optical performance as a function of the pupil of the wearer of the ophthalmic spectacle lens comprising the ophthalmic lens component 100, and of the first and second optical powers of the optical lens system.

With reference to FIG. 3 in step S101 the optical performance parameters obtained for a range of values of optimisation parameter $\phi$ are evaluated. For this purpose a number of values of the optimisation parameter $\phi$ are selected according to the range of variation of the diameter of the pupil PU of the optical system 200. Each selected value of the optimisation parameter $\phi$ corresponds to a diameter or surface area of the central diffractive zone $101\_1$. For each value of optimisation parameter $\phi$ the performance criteria of the optical system at focal points f'1 and f'2 is evaluated over the range of variation of the diameter of the pupil PU of the optical system 200. An average performance parameter value is then obtained for each value of optimisation parameter $\phi$ over the range of PU diameter. In step S102 the mean performance parameters obtained for different values of optimisation parameter $\phi$ are compared with one another to determine the value of optimisation parameter $\phi$ giving the best optical performance. In step S103 the surface area of the central diffractive zone $101\_1$ corresponding to the best optical performance is determined, i.e. corresponding to the optimised optimisation parameter $\phi$ value and the position of the annular diffractive zones $101\_2$ to $101\_n$ are determined accordingly. In step S104 the optical lens component 100 is configured according to the determined surface values of the diffractive zone.

In the particular case where the ophthalmic lens system 200 is a hybrid ophthalmic lens system such as a progressive ophthalmic lens, in which the ophthalmic lens component 100 is placed, a further step S105 involves placing the ophthalmic lens component 100 in the ophthalmic lens system 200, typically in the near vision zone. In the particular case where the ophthalmic lens system 200 is a hybrid progressive lens system the aim is to reduce the peripheral astigmatism of the lens system for a given addition value Add. The placement of a binary bifocal ophthalmic lens component 100 in the near vision zone of a bifocal progressive ophthalmic spectacle lens 200 helps to improve the performance of image transfer outside the central progression corridor of optical power.

Indeed, a progressive lens system of addition value Add has in its peripheral zones of vision an astigmatism Ast linked to the geometry of the lens system and which according to a simplified empirical model varies linearly with the addition Add of the progressive lens system such that $Ast \approx Add$.

Returning to FIGS. 2 and 3 an ophthalmic lens component, for which the optical performance has been optimized in accordance with embodiments of the invention, is placed in the near vision zone NV of a progressive ophthalmic lens of addition $Add-\Delta P$. The ophthalmic lens component 100 is a binary or a diffractive doublet lens having optical powers $\Delta P$ and $0\delta$. Accordingly, the overall hybrid ophthalmic lens 200 obtained has, in a peripheral area, an astigmatism $Ast \approx Add-\Delta P$ and an addition Add. Consequently in the near vision zone NV the user benefits simultaneously from an addition $Add-\Delta P$ and an addition Add. As a result the peripheral astigmatism of the hybrid ophthalmic lens is reduced for a given addition to the detriment of a reduced quality of image in the near vision zone due to the presence of two simultaneous dioptric optical powers.

An example of a calculation for determining the value of performance parameter φ according to an embodiment of the invention for optimising the optical performance of a binary bifocal lens will now be presented. In this example the brightness at focal points f1 and f2 is evaluated as a performance criterion.

Considering a thin lens of transmittance $t_\phi(r, \lambda 0)$ $$t_\phi(r, \lambda_0) = \frac{t_1(r, \lambda_0)e^{i\phi} + t_2(r, \lambda_0)}{|t_1(r, \lambda_0)e^{i\phi} + t_2(r, \lambda_0)|} \quad (1)$$

where φ is a phase term independent of the radius r of the lens which has no effect on the first and second optical powers P1 and P2 of the lens.

The transmittance may also be expressed as $$t_\phi(r, \lambda_0) = \exp\left[-i\pi r^2\left(\frac{P_1 + P_2}{2\lambda_0}\right) + i\frac{\phi}{2}\right]t_{\Delta,\phi}(r, \lambda_0) \quad (2)$$

where:

$$t_{\Delta,\phi}(r, \lambda_0) = \frac{2\cos(\pi r^2 \Delta P/2\lambda_0 - \phi/2)}{|2\cos(\pi r^2 \Delta P/2\lambda_0 - \phi/2)|} = \quad (3)$$

$$\begin{cases} 1 & \text{if } -\frac{\pi}{2}\mod(2\pi) < \frac{\pi r^2 \Delta P}{2\lambda_0} - \phi/2 < \frac{\pi}{2}\mod(2\pi) \\ -1 & \text{if } \frac{\pi}{2}\mod(2\pi) < \frac{\pi r^2 \Delta P}{2\lambda_0} - \phi/2 < \frac{3\pi}{2}\mod(2\pi) \end{cases}$$

It becomes clear from expression (3) that expression (1) represents the transmittance of a doublet made up of a refractive lens of optical power (P1+P2)/2 and of a binary lens of which the two brightest orders of diffraction correspond to optical powers −ΔP/2 and ΔP/2.

At a given wavelength $\lambda \neq \lambda_0$ $$t(r, \lambda) = \exp\left[-i\pi r^2\left(\frac{P_1 + P_2}{2\lambda}\right) + i\frac{\lambda_0}{\lambda}\frac{\phi}{2}\right]t_{\Delta,\phi}(r, \lambda) \quad (4)$$

$$t_{\Delta,\phi}(r, \lambda) = \begin{cases} 1 & \text{if } -\frac{\pi}{2}\mod(2\pi) < \frac{\pi r^2 \Delta P}{2\lambda_0} - \phi/2 < \frac{\pi}{2}\mod(2\pi) \\ \exp\left(\frac{i\pi\lambda}{\lambda_0}\right) & \text{if } \frac{\pi}{2}\mod(2\pi) < \frac{\pi r^2 \Delta P}{2\lambda_0} - \phi/2 < \frac{3\pi}{2}\mod(2\pi) \end{cases} \quad (5)$$

$$\phi_0 = \pi r^2 \Delta P/2\lambda_0 \quad (6)$$

Phase $\psi(\lambda_0)$ of the transmittance $t_{\Delta,\phi}(r, \lambda)$: $t_{\Delta,\phi}(r, \lambda) = \exp[i\psi(\phi_0)]$ is represented graphically in FIG. 4 which shows the influence of the parameter φ on the diameters of the diffraction zones of a binary lens.

Figure 4:
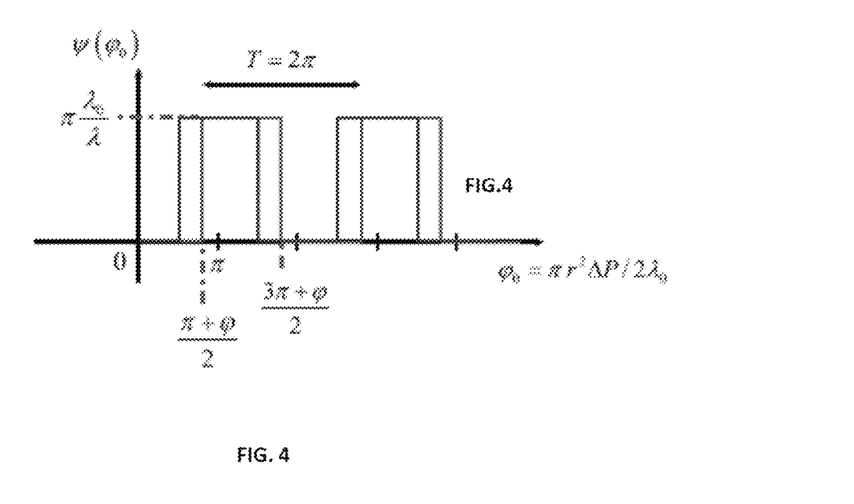
FIG. 4 graphically illustrates the influence of the optimisation parameter φ on the diameters of the diffraction zones of a binary lens, in accordance with at least one embodiment of the invention.
Figure 5:
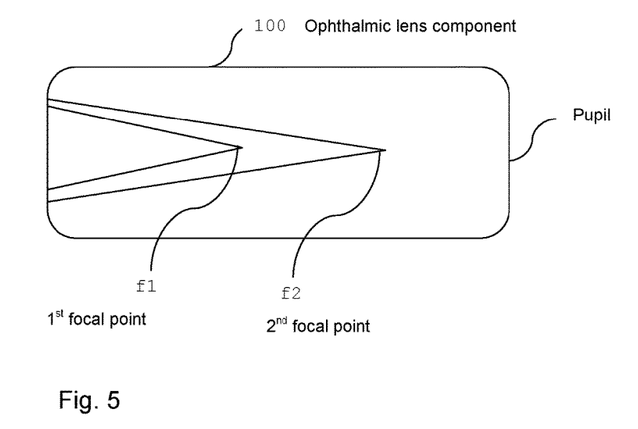
FIG. 5 shows the bifocal lens component and the bifocal optical system.

It is thus shown that variation of the value of optimisation parameter φ corresponds to variation of the diameter of the annular zones making up the binary part of the lens, and in particular that the surface area of the annular areas 101_2 to 101_n surrounding the central area do not change with optimisation parameter φ while the area of the central zone 101_1 does change with optimisation parameter φ. Thus the value of optimization parameter φ can be linked with the diameter of the central zone 101_1.

Adding a constant phase term φ to the transmittance equation (1) corresponds to a translation of the annular diffraction zones of the binary lens. Variation of the diameters of the annular diffraction zones can be used to optimise the optical performance of the lens.

The parameter φ can be optimised thus to improve the optical performances of a binary bifocal lens.

φ being a periodic function of the variable $\phi_0$ of period T=2π, $t_{\Delta,\phi}$ can be decomposed into a Fourier series:

$$t_{\Delta,\phi}(r, \lambda) = \sum_{q=-\infty}^{+\infty} c_q \exp(iq\phi_0) \quad (7)$$

with:

$$c_q = \frac{1}{2\pi}\left[\int_{\frac{\pi}{2}+\frac{\phi}{2}}^{\frac{3\pi}{2}+\frac{\phi}{2}} \exp\left(i\pi\frac{\lambda_0}{\lambda}\right)\exp(-iq\phi_0)d\phi_0 + \int_{\frac{3\pi}{2}+\frac{\phi}{2}}^{\frac{5\pi}{2}+\frac{\phi}{2}} \exp(-iq\phi_0)d\phi_0\right] \quad (8)$$

A binary lens behaves as a lens having an infinite number of focal points associated with dioptric powers $-\lambda q \Delta P/2\lambda^0$ leading to:

$$c_q = \frac{\exp(-iq\phi/2)}{2}\mathrm{sinc}\left(\frac{q}{2}\right)\left[1 + \exp(-iq\pi)\exp\left(i\pi\frac{\lambda_0}{\lambda}\right)\right] \quad (9)$$

Generally the diffraction efficiency associated with the order of diffraction q is referred to as $|c_q|^2$. Here it can be seen that the value of the parameter φ has no influence on $|c_q|^2$.

In a Fresnel approximation the complex amplitude expression associated with the order q on a point of the optical axis situated at a distance z from a lens of pupil Σ of which the transmittance is defined by $t_{\Delta,\phi}(r, \lambda)$ receiving light of a planar wave of unitary amplitude is given as:

$$U'_q(\vec{0}, z) = \frac{\exp(i2\pi z/\lambda)}{i\lambda z}c_q \int\!\!\int_\Sigma \exp\left(iq\pi\frac{r^2 \Delta P}{2\lambda_0}\right)\exp\left(i\pi\frac{r^2}{\lambda z}\right)d^2r \quad (10)$$

If the pupil of the binary lens system is circular and has a diameter A:

$$U'_q(\vec{0}, z) = \quad (11)$$
$$\frac{\exp(i2\pi z/\lambda)}{i\lambda z}c_q\pi\exp\left(iq\pi\frac{A^2\Delta P}{16\lambda_0}\right)\exp\left(i\pi\frac{A^2}{8\lambda z}\right)\frac{A^2}{4}\mathrm{sinc}\left(q\frac{\Delta PA^2}{16\lambda_0} + \frac{A^2}{8\lambda z}\right)$$

In what follows the analysis is limited to two orders of diffraction −1 and 1 having respective efficiencies at wavelength $\lambda = \lambda_0$ is 40.5%. The following is calculated:

$$|U'_1(\vec{0}, z) + U'_{-1}(\vec{0}, z)|^2 = |U'_1(\vec{0}, z)|^2 + |U'_{-1}(\vec{0}, z)|^2 + 2Re[U'_1(\vec{0}, z)^*U'_{-1}(\vec{0}, z)] \quad (12)$$

where Re represents the real part of the complex number.

The optimisation therefore involves making as high as possible the value of $|U'_1(\vec{0}, z) + U'_{-1}(, z)|^2$ so that a maximum amount of light is spread on the optical axis, in particular at the first and second focal points corresponding to the diffraction orders −1 and 1 at the wavelength $\lambda = \lambda_0$. The first and second focal points are respectively situated at z1=2/ΔP and z2=−2/ΔP. For a wavelength of light $\lambda \neq \lambda_0$ the first and second focal points are situated at z1=2λ₀/λΔP and z2=−2λ₀/λΔP. The value of φ is optimized so that in the vicinity of the optical axis at z1=2/ΔP and z2=−2/ΔP interference between diffraction orders −1 and 1 are as constructive as possible and then a maximum amount of light is spread at the first and second focal points. From equations (9) and (11) it is noted that $|U'_q(\vec{0}, z)|^2$ does not depend on the value of $\phi$. Consequently the aim is to increase the value of the term on the right of equation (12) i.e. that the argument of $U'_1(\vec{0}, z)*U'_{-1}(\vec{0}, z)$ is as close as possible to $0 \pmod{2\pi}$. From equation (11) $U'_1(\vec{0}, z)*U'_{-1}(\vec{0}, z)$ is developed and the following result is obtained:

$$U'_1(\vec{0}, z)^* U'_{-1}(\vec{0}, z) = 2\left(\frac{\pi A^2}{8\lambda z}\right)^2 \exp(i\phi)\left[\operatorname{sinc}\left(\frac{1}{2}\right)\right]^2 \left[1 - \cos\left(\frac{\pi \lambda_0}{\lambda}\right)\right] \quad (13)$$

$$\exp\left(-i\pi \frac{A^2 \Delta P}{8\lambda_0}\right) \times \operatorname{sinc}\left(\frac{\Delta P A^2}{16\lambda_0} + \frac{A^2}{8\lambda z}\right) \operatorname{sinc}\left(-\frac{\Delta P A^2}{16\lambda_0} + \frac{A^2}{8\lambda z}\right)$$

At a value of $\pi$ dependent on the sign of the product of the cardinal sinus the argument of $U'_1(\vec{0}, z)*U'_{-1}(\vec{0}, z)$ is:

$$\Delta \phi = \phi - \pi \frac{A^2 \Delta P}{8\lambda_0} \quad (14)$$

And thus the optimal value of factor $\phi$ is:

$$\phi = \pi \frac{A^2}{8\lambda_0} \Delta P(\mathrm{mod} 2\pi) \text{ if } \operatorname{sinc}\left(\frac{\Delta P \cdot A^2}{16\lambda_0} + \frac{A^2}{8\lambda z}\right)\operatorname{sinc}\left(-\frac{A^2 \Delta P}{16\lambda_0} + \frac{A^2}{8\lambda z}\right) > \quad (15)$$

$$0 \text{ with } \operatorname{sinc}(x) = \frac{\sin(\pi \kappa)}{\pi \kappa}$$

$$\phi = \pi + \pi \frac{A^2}{8\lambda_0} \Delta P(\mathrm{mod} 2\pi) \text{ if } \operatorname{sinc}\left(\frac{\Delta P \cdot A^2}{16\lambda_0} + \frac{A^2}{8\lambda z}\right)$$

$$\operatorname{sinc}\left(-\frac{A^2 \Delta P}{16\lambda_0} + \frac{A^2}{8\lambda z}\right) < 0$$

It is noted that at the first and second focal points associated with the orders of diffraction 1 and −1 at a wavelength $\lambda = \lambda_0$ respectively situated at $z1 = 2/\Delta P$ and $z2 = -2/\Delta P$, the optimal value of factor $\phi$ is the same. As a consequence it is possible to optimize the spreading of light at the two focal points F1 and F2 simultaneously. Moreover wavelength $\lambda$ and position z only influence the sign of the cardinal sinuses. Thus in the zones of the spectrum of the nominal wavelength $\lambda_0$ and in the zones of space around $z1 = 2/\Delta P$ and $z2 = -2/\Delta P$ where the sign of the product of the cardinal sinus does not change, the optimal value of factor $\phi$ does not depend on the wavelength $\lambda$ nor on the position Z and remains the same as in the case where the wavelength $\lambda = \lambda_0$ Elsewhere the optimal value of factor $\phi$ is $\pi$.

Use of parameter $\phi$ enables the interferences between the orders of diffraction 1 and −1 along the optical axis to be made more constructive. Consequently if the diameter of the binary lens is great the two focal points are separated and their interference has little influence.

Although the present invention has been described hereinabove with reference to specific embodiments, the present invention is not limited to the specific embodiments, and modifications will be apparent to a skilled person in the art which lie within the scope of the present invention.

For instance, while some specific embodiments have been described above in the context of an ophthalmic lens it will be appreciated that the invention may be applied to other optical substrates used as windows, automotive and aircraft windshields, films, ophthalmic instrumentation, computer monitors, television screens, telephone screens, multimedia display screens, lighted signs, light projectors and light sources, other ophthalmic devices and the like without departing from the scope of the invention. The ophthalmic devices may include eye glasses, sun glasses, goggles or the like.

Many further modifications and variations will suggest themselves to those versed in the art upon making reference to the foregoing illustrative embodiments, which are given by way of example only and which are not intended to limit the scope of the invention, that being determined solely by the appended claims. In particular the different features from different embodiments may be interchanged, where appropriate.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A simultaneously bifocal optical system, the said optical system being defined by a first system focal point and a second system focal point and a pupil, said system comprising:
   a simultaneously bifocal diffractive lens component having a first focal point, a second focal point and a plurality of diffractive zones, the plurality of diffractive zones including a central zone and a plurality of annular concentric zones surrounding the central zone, the lens component having a first optical power P1 and a second optical power P2 associated with the first focal point and the second focal point respectively, the first focal point and the second focal point respectively corresponding to points of convergence of the most luminous orders of diffraction generated by the lens component for a nominal wavelength, the first system focal point and the second system focal point having a position dependent upon a value of the first optical power P1 and the second optical power P2 of the lens respectively, wherein the central zone has a surface area value configured such that a predetermined optical performance optimization parameter $\phi$ is optimized, said optical performance optimization parameter $\phi$ being considered in the vicinity of the first and second system focal points and varying as a function of a surface area value of the central zone without modifying the operational function of the diffractive zones, said predetermined optical performance optimization parameter $\phi$ being such as the brightness and/or the Modulation Transfer Function in the vicinity of the first and second system focal points, whereby the central zone has a surface area value determined as a function of the pupil of the optical system, of the first optical power P1 and of the second optical power P2, and the surface area of the annular zones surrounding the central zone does not change with the optimization parameter $\phi$ while the area of the central zone does change with optimization parameter $\phi$.

2. A system according to claim 1, wherein each of the plurality of diffractive zones has a spherical profile or a binary type profile.

3. A system according to claim 2, wherein the pupil has a variable surface area value.

4. A system according to claim 2, wherein the pupil has a fixed surface area value.

5. A system according to claim 1, wherein the pupil has a variable surface area value.

6. A system according to claim 1, wherein the pupil has a fixed surface area value.

7. A system according to claim 1, wherein the lens component is configured as a contact lens.

8. A system according to claim 1, wherein the lens component is part of an intraocular implant.

9. A system according to claim 1, wherein the lens component constitutes the optical system.

10. A system according to claim 1, wherein the lens component is part of a near vision zone of a progressive, multifocal ophthalmic lens having a complex surface comprising a far vision zone with a far vision reference point, said near vision zone with a near vision reference point, and an intermediate vision zone wherein a main meridian of the progression crosses the three said vision zones, wherein the first optical power P1 differs from the second optical power P2.

11. A system according to claim 10, wherein the lens component comprises a refractive component and a simultaneously bifocal diffractive component in which the refractive component is juxtaposed with the diffractive component and wherein the refractive component has an optical power equal to P1/2+P2/2 and the diffractive component has a first power equal to $\Delta P/2$ and a second power equal to $-\Delta P/2$, where $\Delta P=P1-P2$.

12. A method of determining a simultaneously bifocal diffractive optical system, said optical system being defined by a first system focal point and a second system focal point and a pupil, said system comprising a lens component having a first focal point, a second focal point and a plurality of diffractive zones, the plurality of diffractive zones including a central zone and a plurality of annular concentric zones surrounding the central zone, the lens component having a first optical power P1 and a second optical power P2 associated with the first focal point and the second focal point respectively, the first focal point and the second focal point respectively corresponding to points of convergence of the most luminous orders of diffraction generated by the lens component for a nominal wavelength, the first system focal point and the second system focal point having a position dependent upon the value of the first optical power P1 and the second optical power P2 of the lens respectively, wherein the method comprises:
 a step of determining a surface area value of the central zone by optimization of a predetermined optical performance optimization parameter $\phi$, said optical performance optimization parameter $\phi$ being considered in the vicinity of the first and second system focal points and varying as a function of a surface area value of the central zone without modifying the operational function of the diffractive zones, said predetermined optical performance optimization parameter $\phi$ being such as the brightness and/or the Modulation Transfer Function in a vicinity of the first and second system focal points, whereby the surface area value of the central zone is determined as a function of the pupil of the optical system, of the first optical power P1 and of the second optical power P2,and the surface area of the annular zones surrounding the central zone does not change with the optimization parameter $\phi$ while the area of the central zone does change with optimization parameter $\phi$.

13. A method according to claim 12, wherein the component constitutes the optical system.

14. A method according to claim 13, wherein the pupil of the optical system has a surface area value variable within a range of surface area values and wherein the step of determining the surface area value of the central zone comprises:
 evaluating surface area values of the central zone, associated with a set of pupils of the said optical system, each pupil having a surface area value within the said range of surface area values, by optimization of the optical performance optimization parameter $\phi$ for each pupil of this set;
 evaluating an optical performance of the optical system for each of the surface area values of the central zone as a mean of the optimized optical performance optimization parameters $\phi$ on the set of pupil surface area values of the said optical system; and
 determining an optimum performance among the evaluated optical performances of the said optical system and deducing therefrom the surface area value of the central zone which corresponds to the determined optimum performance.

15. A method according to claim 14, wherein the optical performance optimization parameter $\phi$ is based on the Modulation Transfer Functions at the system focal planes associated with the first and second focal points.

16. A method according to claim 12, wherein the pupil of the optical system has a fixed surface area value and the step of determining the surface area value of the central zone by optimization of the optical performance optimization parameter $\phi$ is carried out in considering the pupil surface area value.

17. A method according to claim 12, wherein the pupil of the optical system has a surface area value variable within a range of surface area values and wherein the step of determining the surface area value of the central zone comprises:
 evaluating surface area values of the central zone, associated with a set of pupils of the said optical system, each pupil having a surface area value within the said range of surface area values, by optimization of the optical performance optimization parameter $\phi$ for each pupil of this set;
 evaluating an optical performance of the optical system for each of the surface area values of the central zone as a mean of the optimized optical performance optimization parameters $\phi$ on the set of pupil surface area values of the said optical system; and
 determining an optimum performance among the evaluated optical performances of the said optical system and deducing there from the surface area value of the central zone which corresponds to the determined optimum performance.

18. A method according to claim 17, wherein the optical performance optimization parameter $\phi$ is based on the Modulation Transfer Functions at the system focal planes associated with the first and second focal points.

19. A non-transitory programmable apparatus, the computer program product comprising a sequence of instructions for implementing a method according to claim 12 when loaded into and executed by the programmable apparatus.

* * * * *